United States Patent
Schnabel et al.

(10) Patent No.: US 9,198,412 B2
(45) Date of Patent: Dec. 1, 2015

(54) METHOD FOR ENHANCING THE PERFORMANCE OF A PESTICIDE WITH GUANIDINES

(75) Inventors: Gerhard Schnabel, Elsenfeld (DE); Marc Nolte, Mannheim (DE); Mariano Ignacio Etcheverry, Mannheim (DE); Gerhard Genari, Limburgerhof (DE); Thomas Kroehl, Schriesheim (DE); Matthias Bratz, Maxdorf (DE); Terrance Cannan, Raleigh, NC (US); Steven Bowe, Apex, NC (US); Chad Brommer, Raleigh, NC (US); John Frihauf, Raleigh, NC (US); Charles W. Finch, Garner, NC (US); Walter Thomas, Fuquay-Varina, NC (US)

(73) Assignee: BASF SE, Ludwigshafen (DE)

( * ) Notice: Subject to any disclaimer, the term of this patent is extended or adjusted under 35 U.S.C. 154(b) by 12 days.

(21) Appl. No.: 14/115,222

(22) PCT Filed: Apr. 25, 2012

(86) PCT No.: PCT/EP2012/057578
§ 371 (c)(1),
(2), (4) Date: Nov. 1, 2013

(87) PCT Pub. No.: WO2012/150162
PCT Pub. Date: Nov. 8, 2012

(65) Prior Publication Data
US 2014/0066309 A1   Mar. 6, 2014

Related U.S. Application Data

(60) Provisional application No. 61/481,274, filed on May 2, 2011.

(30) Foreign Application Priority Data

May 5, 2011   (EP) ..................... 11164972

(51) Int. Cl.
*A01N 25/00*   (2006.01)
*A01N 25/22*   (2006.01)
*A01N 25/30*   (2006.01)
*A01N 37/40*   (2006.01)
*A01N 47/44*   (2006.01)

(52) U.S. Cl.
CPC ............... *A01N 25/00* (2013.01); *A01N 25/30* (2013.01); *A01N 47/44* (2013.01)

(58) Field of Classification Search
CPC ....... A01N 25/00; A01N 25/22; A01N 25/30; A01N 37/40; A01N 47/44
See application file for complete search history.

(56) References Cited

U.S. PATENT DOCUMENTS 6,184,182 B1   2/2001   Gillespie et al.

FOREIGN PATENT DOCUMENTS

| EP | 0 375 624 | 6/1990 |
|----|-----------|--------|
| EP | 0 988 790 | 3/2000 |
| WO | WO 2010/051435 | 5/2010 |
| WO | WO 2011/008453 | 1/2011 |
| WO | WO 2011/039172 | 4/2011 |
| WO | WO 2011/101303 | 8/2011 |
| WO | WO 2011/113786 | 9/2011 |

OTHER PUBLICATIONS

International Search Report dated Aug. 8, 2012, prepared in International Application No. PCT/EP2012/057578.
International Preliminary Report on Patentability dated 00/05/2013, prepared in International Application No. PCT/EP2012/057578.

*Primary Examiner* — John Pak
*Assistant Examiner* — Nathan W Schlientz
(74) *Attorney, Agent, or Firm* — Brinks Gilson & Lione

(57) ABSTRACT

The present invention relates to a method for enhancing the performance of a pesticide comprising the step of contacting an adjuvant and the pesticide, wherein the pesticide is present in a concentration of less than 10 wt % in the resulting composition containing the adjuvant and the pesticide, and wherein the adjuvant contains a guanidine of formula (A) as defined below, and/or a salt thereof. The invention also relates to a composition comprising an auxin-herbicide and said adjuvant; to a use of said adjuvant for enhancing the performance of a pesticide; and to a method of controlling undesired vegetation, which comprises allowing a herbicidal effective amount of said composition to act on plants, their habitat or on seed of said plants.

16 Claims, No Drawings

METHOD FOR ENHANCING THE PERFORMANCE OF A PESTICIDE WITH GUANIDINES

This application is a National Stage application of International Application No. PCT/EP2012/057578, filed Apr. 25, 2012, which claims the benefit of U.S. Provisional Application No. 61/481,274, filed May 2, 2011, the entire contents of which are hereby incorporated herein by reference. This application also claims priority under 35 U.S.C. §119 to European Patent Application No. 11164972.9, filed May 5, 2011, the entire contents of which is hereby incorporated herein by reference.

The present invention relates to a method for enhancing the performance of a pesticide comprising the step of contacting an adjuvant and the pesticide, wherein the adjuvant contains a guanidine of formula (A) as defined below, and/or a salt thereof. The invention also relates to a composition comprising an auxin-herbicide and said adjuvant; to a use of said adjuvant for enhancing the performance of a pesticide; and to a method of controlling undesired vegetation, which comprises allowing a herbicidal effective amount of said composition to act on plants, their habitat or on seed of said plants. The preferred embodiments of the invention mentioned herein below have to be understood as being preferred either independently from each other or in combination with one another.

Various methods for enhancing the performance of pesticides are known:

WO 2011/039172 discloses a method for preparing a salt of a anionic pesticide and a cationic polyamine. The polyamine reduced the volatility of the anionic pesticide.

WO 2011/008453 discloses guanidine derivatives of glyphosate.

EP 0 988 790 discloses a fungicidal composition comprising synergistically effective amounts of azolopyrimidine derivatives and at least one further fungicide, such as dodine (dodecylguanidine).

The known adjuvants still may be further improved in order to further enhance the performance of pesticides.

Object of the present invention was to find a method to enhance the performance of a pesticide. Another object was to reduce the volatility of a pesticide and/or the biological efficacy of a pesticide.

The object was solved by a method for enhancing the performance of a pesticide comprising the step of contacting an adjuvant and the pesticide, wherein the pesticide is present in a concentration of less than 10 wt % in the resulting composition containing the adjuvant and the pesticide, and wherein the adjuvant contains a guanidine of the formula (A)

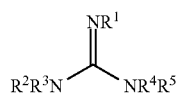

and/or a salt thereof, wherein
$R^1$, $R^2$, $R^3$, $R^4$, and $R^5$ are independently H, $C_1$-$C_{30}$-alkyl, $C_2$-$C_{15}$-alkandiyl, $C_2$-$C_{30}$-alkenyl, $C_6$-$C_{12}$-aryl, $C_7$-$C_{30}$-alkylaryl, —$(CH_2)_m$—$(NR^6(CH_2)_n)_x$—$NR^7R^8$ or —$(CH_2)_m$—$CH(NH_2)CH(NH_2)R^8$, polyethyleneimino, or heterosubstituted derivatives thereof;
$R^6$ and $R^7$ are independently hydrogen or $C_1$-$C_6$-alkyl;
$R^8$ is $C_1$-$C_{30}$ alkyl or —$C(NH)NH_2$; and
m, n and x are independently an integer from 1 to 10.

The term heterosubstituted derivatives refers to derivatives of $C_1$-$C_{30}$-alkyl, $C_2$-$C_{15}$-alkandiyl, $C_2$-$C_{30}$-alkenyl, $C_6$-$C_{12}$-aryl, $C_7$-$C_{30}$-alkylaryl, —$(CH_2)_m$—$(NR^6(CH_2)_n)_x$—$NR^7R^8$ or —$(CH_2)_m$—$CH(NH_2)CH(NH_2)R^8$, or polyethyleneimino, wherein at least one carbon atom is substituted by at least one heteroatom (e.g. O, N, or S) containing functional group. Examples for heteroatom containing functional groups are keto, aldehyde, amine, hydroxy, or thiol groups, wherein keto, hydroxy and amine are preferred. Preferred are heterosubstituted derivatives of $C_1$-$C_{30}$-alkyl and $C_2$-$C_{15}$-alkandiyl, especially keto, hydroxy and/or amine-substituted derivatives of $C_1$-$C_{30}$-alkyl and $C_2$-$C_{15}$-alkandiyl.

The term $C_2$-$C_{15}$-alkandiyl typically refers to a cyclic guanidine of the formula (A), wherein two residues selected from $R^1$, $R^2$, $R^3$, $R^4$, and $R^5$ form together the $C_2$-$C_{15}$-alkandiyl. For example, in triazabicyclodecene (1,5,7-Triazabicyclo[4.4.0]dec-5-ene or TBD) $R^1$ and $R^2$ form together a 1,3-propandiyl group,) $R^3$ and $R^4$ form together a 1,3-propandiyl group, and $R^5$ is H.

The term heterosubstituted $C_2$-$C_{15}$-alkandiyl typically refers to a cyclic guanidine of the formula (A), wherein two residues selected from $R^1$, $R^2$, $R^3$, $R^4$, and $R^5$ form together the heterosubstituted $C_2$-$C_{15}$-alkandiyl. For example, in creatinine (also known as 2-imino-1-methylimidazolidin-4-on) $R^1$ is H, $R^2$ is methyl, $R^4$ is H, and $R^3$ and $R^5$ form together a 1,2-ethandiyl group, which is substituted by a keto group.

Preferably, $R^1$ is H, $C_1$-$C_{30}$-alkyl, $C_2$-$C_{30}$-alkenyl, $C_6$-$C_{12}$-aryl, $C_7$-$C_{30}$-alkylaryl, —$(CH_2)_m$—$(NR^6(CH_2)_n)_x$—$NR^7R^8$ or —$(CH_2)_m$—$CH(NH_2)CH(NH_2)R^8$, or polyethyleneimino; and $R^2$, $R^3$, $R^4$, and $R^5$ are independently H, $C_1$-$C_{22}$-alkyl, or $C_1$-$C_{22}$-alkenyl. More preferably, $R^1$ is H, $C_1$-$C_{30}$-alkyl, $C_2$-$C_{30}$-alkenyl, $C_6$-$C_{12}$-aryl, $C_7$-$C_{30}$-alkylaryl, —$(CH_2)_m$—$(NR^6(CH_2)_n)_x$—$NR^7R^8$ or —$(CH_2)_m$—$CH(NH_2)CH(NH_2)R^8$, or polyethyleneimino; and $R^2$, $R^3$, $R^4$, and $R^5$ are H.

In another preferred form, $R^1$ is H, $C_1$-$C_{30}$-alkyl, $C_2$-$C_{30}$-alkenyl, $C_6$-$C_{12}$-aryl, $C_7$-$C_{30}$-alkylaryl, —$(CH_2)_m$—$(NR^6(CH_2)_n)_x$—$NR^7R^8$ or —$(CH_2)_m$—$CH(NH_2)CH(NH_2)R^8$, polyethyleneimino or heterosubstituted derivatives thereof; and $R^2$, $R^3$, $R^4$, and $R^5$ are independently H, $C_1$-$C_{22}$-alkyl, $C_2$-$C_{10}$-alkandiyl, $C_1$-$C_{22}$-alkenyl, or heterosubstituted derivatives thereof. More preferably, $R^1$ is H, $C_1$-$C_{30}$-alkyl, $C_2$-$C_{30}$-alkenyl, $C_6$-$C_{12}$-aryl, $C_7$-$C_{30}$-alkylaryl, —$(CH_2)_m$—$(NR^6(CH_2)_n)_x$—$NR^7R^8$ or —$(CH_2)_m$—$CH(NH_2)CH(NH_2)R^8$, polyethyleneimino, or heterosubstituted derivatives thereof; and $R^2$, $R^3$, $R^4$, and $R^5$ are H or $C_2$-$C_6$-alkandiyl, or heterosubstituted derivatives thereof.

In some embodiments, $R^1$, $R^2$, $R^3$, $R^4$, and $R^5$ are independently H or $C_1$-$C_{30}$ alkyl, such as $C_1$-$C_4$ alkyl or $C_1$-$C_3$ alkyl. In some further embodiments, $R^1$, $R^2$, $R^3$, $R^4$, and $R^5$ are independently H, $C_2$-$C_{10}$-alkandiyl, or $C_1$-$C_{30}$ alkyl, or heterosubstituted derivatives thereof.

Most preferably $R^1$, $R^2$, $R^3$, $R^4$, and $R^5$ are independently methyl or H, especially H.

In some embodiments, $R^1$, $R^2$, $R^3$, $R^4$, and $R^5$ independently may be a $C_8$-$C_{30}$ alkyl or alkenyl group, preferably $C_{12}$-$C_{18}$ alkyl or $C_{12}$-$C_{18}$ alkenyl. Representative alkyl groups include octyl, nonyl, decyl, undecyl, dodecyl, tridecyl, tetradecyl, pentadecyl, hexadecyl, heptadecyl, octadecyl, coco, and tallow. Representative alkenyl groups include octenyl, nonenyl, decenyl, undecenyl, dodecenyl, tridecenyl, tetradecenyl, pentadecenyl, hexadecenyl, heptadecenyl, and octadecenyl.

In some other embodiments, $R^1$, $R^2$, $R^3$, $R^4$, and $R^5$ independently may be —$(CH_2)_m$—$CH(NH_2)CH(NH_2)R^8$, m is 1 and $R^8$ is a $C_8$-$C_{30}$ alkyl or alkenyl group such as those listed above. In some embodiments, $R^1$, $R^2$, $R^3$, $R^4$, and $R^5$ independently may be —$(CH_2)_m$—$(NR^6(CH_2)_n)_x$—$NR^7R^8$, $R^6$ and $R^7$ are hydrogen, $R^8$ is a $C_8$-$C_{30}$ alkyl or $C_8$-$C_{30}$ alkenyl group such as those listed above, m and n are 2, and x is an integer from 1 to 5.

Specific examples of a guanidine of the formula (A) are guanidine; 2-dodecyl guanidine; 2-hexadecyl guanidine; ($C_{12-18}$-hydrocarbyl) guanidine; N,N,N,N-tetramethyl-($C_{12-18}$-hydrocarbyl) guanidine; N,N,N,N-tetramethyl-($C_{12}$-hydrocarbyl)guanidine; 2-($C_{12}$-hydrocarbyl)guanidine; 2-3,6,9,12,15,18-hexaazatriacontyl guanidine; 1,1,3,3-tetramethyl-2-3,6,9,12,15,18-hexaazatriacontyl guanidine; (Z)-1,1,3,3-tetramethyl-2-(octadec-9-enyl)guanidine; 2-hexadecyl-1,1,3,3-tetramethyl guanidine; 2-(2,3-diaminopropyl)($C_{12-18}$-hydrocarbyl)guanidine; 2-(2,3-diaminopropyl)($C_{12-18}$-hydrocarbyl)-1,1,3,3-tetramethyl guanidine; N-(1,1-diamino-2,5,8,11,14,17-hexaazanonadec-1-en-19-yl)heptadecanamide; dodine; guatazine; iminoctadine; and the salts thereof, wherein the salts are preferred. Further specific examples of a guanidine of the formula (A) are triazabicyclodecene, arginine, creatinine and creatin, and the salts thereof, wherein the salts are preferred. Preferred examples of a guanidine of the formula (A) are guanidine ($R^1$, $R^2$, $R^3$, $R^4$, and $R^5$ are H), dodine, iminoctadine, and the salts thereof, wherein the salts are preferred. Especially preferred guanidine of formula (A) is guanidine and the salts thereof, wherein the salts are preferred. In another especially preferred form, the formula (A) is triazabicyclodecene, and the salts thereof, wherein the salts are preferred. In another especially preferred form, the formula (A) is arginine, and the salts thereof, wherein the salts are preferred. In another especially preferred form, the formula (A) is creatinine and the salts thereof, wherein the salts are preferred. In another especially preferred form, the formula (A) is creatin, and the salts thereof, wherein the salts are preferred.

In a preferred embodiment the adjuvant contains a salt of the guanidine of the formula (A). In a further preferred embodiment the adjuvant contains a salt of the guanidine of the formula (A) as well as the guanidine of the formula (A).

The term "salt" refers to chemical compounds, which comprise at least one anion and at least one cation. The ratio of anions to cations usually depends on the electric charge of the ions and will result in neutral salts. Typically, salts dissociate in anions and cations when dissolved in water.

A salt of the guanidine of the formula (A) comprises usually a guanidinium cation as represented by the following formula:

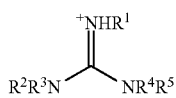

The salt of the guanidine of the formula (A) usually comprises said guanidinium cation and an anionic counterion. Suitable anionic counterions may be derived from an inorganic acid or an organic acid, wherein inorganic acids are preferred.

Examples for organic acids are monocarboxylic acids (e.g. formic acid, acetic acid, propionic acid, butyric acid, isobutyric acid, hexanoic acid, heptanoic acid, octanoic acid, nonanoic acid, decanoic acid, lauric acid, myristic acid, palmitic acid, stearic acid, acrylic acid, methacrylic acid, crotonic acid, isocrotonic acid, phenylacetic acid, cinnamic acid, benzoic acid, sorbic acid, nicotinic acid, urocanic acid and pyrrolidone-carboxylic acid); dicarboxylic acids (e.g. oxalic acid, malonic acid, succinic acid, glutamic acid, adipic acid, pimelic acid, cork acid, azelaic acid, sebacic acid, maleic acid, fumaric acid, phthalic acid and terephthalic acid); hydroxy acids (e.g. glycolic acid, lactic acid, malic acid, tartaric acid, citric acid and hydroxybenzoic acid); amino acids (e.g. glycine, alanine, β-alanine, valine, leucine, phenylalanine, tyrosine, serine, threonine, methionine, cysteine, cystine, proline, hydroxyproline, pipecolic acid, tryptophan, aspartic acid, asparagine, glutamic acid, glutamine, lysine, histidine, ornithine, arginine and aminobenzoic acid); lower alkylsulfonic acids (e.g. methanesulfonic acid and trifluoromethanesulfonic acid); arylsulfonic acids (e.g. benzenesulfonic acid and p-toluenesulfonic acid).

Examples for inorganic acids are hydrohalogenic acids (e.g. hydrofluoric acid, hydrochloric acid, hydrobromic acid and hydroiodic acid) and inorganic acids (e.g. perchloric acid, sulfuric acid, nitric acid, phosphoric acid and carbonic acid).

More preferred anionic counterions are selected from sulfate, hydrogensulfate, phosphate, dihydrogenphosphate, monohydrogenphosphate, hydrocarbonate, carbonate, sulfamate, chloride, nitrate, thiocyanate. Especially preferred anionic counterions are hydrogensulfate, phosphate, dihydrogenphosphate, monohydrogenphosphate, hydrocarbonate, and carbonate.

Preferred salts of the guanidine of the formula (A) are guanidine sulfate, guanidine sulfamate, guanidine hydrogensulfate, guanidine phosphate, guanidine dihydrogenphosphate, guanidine monohydrogenphosphate, guanidine hydrocarbonate, guanidine carbonate, guanidine chloride, guanidine nitrate, guanidine thiosulfat, guanidine thiocyanate. Especially preferred are guanidine hydrogensulfate, guanidine phosphate, guanidine dihydrogenphosphate, guanidine monohydrogenphosphate, guanidine hydrocarbonate, guanidine sulfate, and guanidine carbonate.

Typically, the guanidine of the formula (A) or the salt thereof are soluble in water. Preferably, their solubility in water at 20° C. is at least 1 wt %, more preferably at least 5 wt %, and in particular at least 10 wt %.

Typically, the adjuvant which contains a guanidine of the formula (A) is a solid. Preferably, the adjuvant is solid at 20° C. Typically, the guanidine of the formula (A) is a solid. Preferably, the guanidine of the formula (A) is solid at 20° C.

Typically, the adjuvant contains at least 50 wt %, preferably at least 90 wt %, and in particular at least 98 wt % of the guanidine of the formula (A). In another form, the adjuvant consists of the guanidine of the formula (A).

The term "pesticide" within the meaning of the invention states that one or more compounds can be selected from the group consisting of fungicides, insecticides, nematicides, herbicide and/or safener or growth regulator, preferably from the group consisting of fungicides, insecticides or herbicides, most preferably from the group consisting of herbicides. Also mixtures of pesticides of two or more the aforementioned classes can be used. The skilled artisan is familiar with such pesticides, which can be, for example, found in the Pesticide Manual, 15th Ed. (2009), The British Crop Protection Council, London.

Examples for Fungicides are:
A) Strobilurins
  azoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, methyl(2-chloro-5-[1-(3-methylbenzyloxyimino)ethyl]benzyl) carbamate and 2-(2-(3-(2,6-dichlorophenyl)-1-methyl-allylideneaminooxymethyl)-phenyl)-2-methoxyimino-N-methyl-acetamide;

B) Carboxamides
- carboxanilides: benalaxyl, benalaxyl-M, benodanil, bixafen, boscalid, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(3',4',5'-trifluorobiphenyl-2-yl)-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide and N-(2-(1,3,3-trimethyl-butyl)-phenyl)-1,3-dimethyl-5-fluoro-1H-pyrazole-4-carboxamide;
- carboxylic morpholides: dimethomorph, flumorph, pyrimorph;
- benzoic acid amides: flumetover, fluopicolide, fluopyram, zoxamide;
- other carboxamides: carpropamid, dicyclomet, mandipromaid, oxytetracyclin, silthiofarm and N-(6-methoxy-pyridin-3-yl)cyclopropanecarboxylic acid amide;

C) Azoles
- triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole;
- imidazoles: cyazofamid, imazalil, pefurazoate, prochloraz, triflumizol;
- benzimidazoles: benomyl, carbendazim, fuberidazole, thiabendazole;
- others: ethaboxam, etridiazole, hymexazole and 2-(4-chloro-phenyl)-N-[4-(3,4-dimethoxyphenyl)-isoxazol-5-yl]-2-prop-2-ynyloxy-acetamide;

D) Heterocyclic Compounds
- pyridines: fluazinam, pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine;
- pyrimidines: bupirimate, cyprodinil, diflumetorim, fenarimol, ferimzone, mepanipyrim, nitrapyrin, nuarimol, pyrimethanil;
- piperazines: triforine;
- pyrroles: fenpiclonil, fludioxonil;
- morpholines: aldimorph, dodemorph, dodemorph-acetate, fenpropimorph, tridemorph;
- piperidines: fenpropidin;
- dicarboximides: fluoroimid, iprodione, procymidone, vinclozolin;
- non-aromatic 5-membered heterocycles: famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester;
- others: acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propyl-chromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo[1,5-a]pyrimidine;

E) carbamates
- thio- and dithiocarbamates: ferbam, mancozeb, maneb, metam, methasulphocarb, metiram, propineb, thiram, zineb, ziram;
- carbamates: benthiavalicarb, diethofencarb, iprovalicarb, propamocarb, propamocarb hydrochlorid, valifenalate and N-(1-(1-(4-cyano-phenyl)ethanesulfonyl)-but-2-yl)carbamic acid-(4-fluorophenyl)ester;

F) Other Active Substances
- guanidines: guanidine, dodine, dodine free base, guazatine, guazatine-acetate, iminoctadine, iminoctadine-triacetate, iminoctadine-tris(albesilate);
- antibiotics: kasugamycin, kasugamycin hydrochloride-hydrate, streptomycin, polyoxine, validamycin A;
- nitrophenyl derivates: binapacryl, dinobuton, dinocap, nitrthal-isopropyl, tecnazen,
- organometal compounds: fentin salts, such as fentin-acetate, fentin chloride or fentin hydroxide;
- sulfur-containing heterocyclyl compounds: dithianon, isoprothiolane;
- organophosphorus compounds: edifenphos, fosetyl, fosetyl-aluminum, iprobenfos, phosphorous acid and its salts, pyrazophos, tolclofos-methyl;
- organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methylbenzenesulfonamide;
- inorganic active substances: Bordeaux mixture, copper acetate, copper hydroxide, copper oxychloride, basic copper sulfate, sulfur;
- others: biphenyl, bronopol, cyflufenamid, cymoxanil, diphenylamin, metrafenone, mildiomycin, oxin-copper, prohexadione-calcium, spiroxamine, tebufloquin, tolylfluanid, N-(cyclo-propylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydronaphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

Examples for Growth Regulators are:
Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole.

Examples for Herbicides are:
- acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
- amino acid derivatives: bilanafos, glyphosate (e.g. glyphosate free acid, glyphosate ammonium salt, glyphosate isopropylammonium salt, glyphosate trimethylsulfonium salt, glyphosate potassium salt, glyphosate dimethylamine salt), glufosinate, sulfosate;
- aryloxyphenoxypropionates: clodinafop, cyhalofop-butyl, fenoxaprop, fluazifop, haloxyfop, metamifop, propaquizafop, quizalofop, quizalofop-P-tefuryl;
- Bipyridyls: diquat, paraquat;
- (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
- cyclohexanediones: butroxydim, clethodim, cycloxydim, profoxydim, sethoxydim, tepraloxydim, tralkoxydim;
- dinitroanilines: benfluralin, ethalfluralin, oryzalin, pendimethalin, prodiamine, trifluralin;
- diphenyl ethers: acifluorfen, aclonifen, bifenox, diclofop, ethoxyfen, fomesafen, lactofen, oxyfluorfen;
- hydroxybenzonitriles: bomoxynil, dichlobenil, ioxynil;
- imidazolinones: imazamethabenz, imazamox, imazapic, imazapyr, imazaquin, imazethapyr;
- phenoxy acetic acids: clomeprop, 2,4-dichlorophenoxyacetic acid (2,4-D), 2,4-DB, dichlorprop, MCPA, MCPA-thioethyl, MCPB, Mecoprop;
- pyrazines: chloridazon, flufenpyr-ethyl, fluthiacet, norflurazon, pyridate;
- pyridines: aminopyralid, clopyralid, diflufenican, dithiopyr, fluridone, fluoroxypyr, picloram, picolinafen, thiazopyr;
- sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;
- triazines: ametryn, atrazine, cyanazine, dimethametryn, ethiozin, hexazinone, metamitron, metribuzin, prometryn, simazine, terbuthylazine, terbutryn, triaziflam;
- ureas: chlorotoluron, daimuron, diuron, fluometuron, isoproturon, linuron, methabenzthiazuron, tebuthiuron;
- other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;
- others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methylphenoxy)-pyridazin-4-ol, 4-amino-3-chloro-6-(4-chlorophenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

Examples for Insecticides are:
- organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
- carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
- pyrethroids: allethrin, bifenthrin, cyfluthrin, cyhalothrin, cyphenothrin, cypermethrin, alphacypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
- insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
- nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;
- GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;
- macrocyclic lactone insecticides: abamectin, emamectin, milbemectin, lepimectin, spinosad, spinetoram;
- mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumezone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

The pesticide is preferably selected from anionic pesticides. The term "anionic pesticide" refers to a pesticide, which is present as an anion. Preferably, anionic pesticides relate to pesticides comprising a protonizable hydrogen. More preferably, anionic pesticides relate to pesticides comprising a carboxylic, thiocarbonic, sulfonic, sulfinic, thiosulfonic or phosphorous acid group, especially a carboxylic acid group. The aforementioned groups may be partly present in neutral form including the protonizable hydrogen.

Usually, anionic pesticides comprise at least one anionic group. Preferably, the anionic pesticide comprises one or two anionic groups. In particular the anionic pesticide comprises exactly one anionic group. An example of an anionic group is a carboxylate group (—C(O)O$^-$). The aforementioned anionic groups may be partly present in neutral form including the protonizable hydrogen. For example, the carboxylate group may be present partly in neutral form of carboxylic acid (—C(O)OH). This is preferably the case in aqueous compositions, in which an equilibrium of carboxylate and carboxylic acid may be present.

Suitable anionic pesticides are given in the following. In case the names refer to a neutral form or a salt of the anionic pesticide, the anionic form of the anionic pesticides are meant. For example, the anionic form of dicamba may be represented by the following formula:

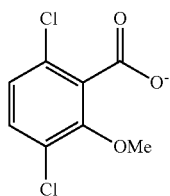 [SMILES: COc1c(Cl)ccc(Cl)c1C(=O)[O-]]

As another example, the anionic form of glyphosate may be represented by at least one of the following formulae:

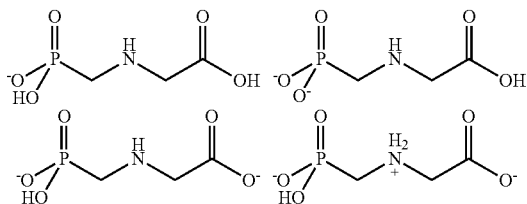

It is known to an expert, that the dissociation of the functional groups and thus the location of the anionic charge may depend for example on the pH, when the anionic pesticides is present in dissolved form. The acid dissociation constants $pK_a$ of glyphosate are typically 0.8 for the first phosphonic acid, 2.3 for the carboxylic acid, 6.0 for the second phosphonic acid, and 11.0 for the amine.

Suitable anionic pesticides are herbicides, which comprise a carboxylic, thiocarbonic, sulfonic, sulfinic, thiosulfonic or phosphorous acid group, especially a carboxylic acid group. Examples are aromatic acid herbicides, phenoxycarboxylic acid herbicides or organophosphorus herbicides comprising a carboxylic acid group.

Suitable aromatic acid herbicides are benzoic acid herbicides, such as diflufenzopyr, naptalam, chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, clopyralid, picloram; quinolinecarboxylic acid herbicides, such as quinclorac, quinmerac; or other aromatic acid herbicides, such as aminocyclopyrachlor. Preferred are benzoic acid herbicides, especially dicamba.

Suitable phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxyphenoxypropionic herbicides, such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop. Preferred are phenoxyacetic herbicides, especially MCPA.

Suitable organophosphorus herbicides comprising a carboxylic acid group are bialafos, glufosinate, glufosinate-P, glyphosate. Preferred is glyphosate.

Suitable other herbicides comprising a carboxylic acid are pyridine herbicides comprising a carboxylic acid, such as fluoroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron; imidazolinone herbicides, such as imazamethabenz, imazamethabenz, imazamox, imazapic, imazapyr, imazaquin and imazethapyr; triazolinone herbicides such as flucarbazone, propoxycarbazone and thiencarbazone; aromatic herbicides such as acifluorfen, bifenox, carfentrazone, flufenpyr, flumiclorac, fluoroglycofen, fluthiacet, lactofen, pyraflufen. Further on, chlorflurenol, dalapon, endothal, flamprop, flamprop-M, flupropanate, flurenol, oleic acid, pelargonic acid, TCA may be mentioned as other herbicides comprising a carboxylic acid.

Suitable anionic pesticides are fungicides, which comprise a carboxylic, thiocarbonic, sulfonic, sulfinic, thiosulfonic or phosphorous acid group, especially a carboxylic acid group. Examples are polyoxin fungicides, such as polyoxorim.

Suitable anionic pesticides are insecticides, which comprise a carboxylic, thiocarbonic, sulfonic, sulfinic, thiosulfonic or phosphorous acid group, especially a carboxylic acid group. Examples are thuringiensin.

Suitable anionic pesticides are plant growth regulator, which comprise a carboxylic, thiocarbonic, sulfonic, sulfinic, thiosulfonic or phosphorous acid group, especially a carboxylic acid group. Examples are 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, preferably prohexadione and trinexapac.

Preferred anionic pesticides are anionic herbicides, more preferably dicamba, glyphosate, 2,4-D, aminopyralid, aminocyclopyrachlor and MCPA. Especially preferred are dicamba and glyphosate. In another preferred embodiment, dicamba is preferred. In another preferred embodiment, 2,4-D is preferred. In another preferred embodiment, glyphosate is preferred. In another preferred embodiment, MCPA is preferred.

In a further embodiment, the pesticide comprises a first anionic pesticide and a second anionic pesticide. For example, the second anionic pesticide is an anionic pesticide wherein at least one anionic group of said anionic pesticide is selected from one or more phosphonate groups. Preferred are herbicides, wherein at least one anionic group of said herbicide is selected from one or more phosphonate groups. Examples are organophosphorus herbicides comprising a carboxylic acid group. Suitable organophosphorus herbicides comprising a carboxylic acid group are bilanafos, glufosinate, glufosinate-P, glyphosate. Preferred is second anionic pesticide is glyphosate.

Preferably, the first anionic pesticide contains a carboxylic acid group, and the second anionic pesticide contains a phosphonate group. More preferably, the first anionic pesticide is an aromatic acid herbicide or a phenoxycarboxylic acid herbicide, and the second anionic pesticide is an organophosphorus herbicide comprising a carboxylic acid group. In another preferred embodiment, the first and the second anionic pesticide are selected from dicamba, quinclorac, glyphosate, 2,4-D, aminopyralid and MCPP. For example the first and the second anionic pesticide are dicamba and glyphosate, 2,4-D and dicamba, dicamba and MCPP, 2,4-D and MCPP, or 2,4-D and glyphosate.

In another preferred embodiment, the pesticide comprises an auxin-herbicide. Various synthetic and natural auxin herbicides are known, wherein synthetic auxin herbicides are preferred.

Examples for natural auxin herbicides are indole-3acetic acid (IAA), phenyl acetic acid (PAA), 4-chloroindole-3-acetic acid (4-Cl-IAA), and indole-3-butanoic acid (IBA).

Examples for synthetic auxin herbicides are 2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters.

Preferred auxin herbicides are 2,4-D and its salts and esters, and dicamba and its salts and esters, wherein 2,4-D and dicamba are more preferred.

The method for enhancing the performance of a pesticide comprises the step of contacting an adjuvant and the pesticide. The composition which results from this step may contain the adjuvant and the pesticide. Any compositions which contain the adjuvant and the pesticide are called herein an "adjuvanted composition". The contacting of the adjuvant and the pesticide may be accomplished by mixing in any order.

Preferably, the method according to the invention comprises the step of contacting the adjuvant and the pesticide, wherein the resulting composition containing the adjuvant and the pesticide is a sprayable aqueous composition.

In another preferred embodiment, the method according to the invention comprises the steps of
a) contacting the pesticide and auxiliaries (resulting in a so called "agrochemical formulation"), followed by
b) contacting the agrochemical formulation and the adjuvant (resulting in an adjuvanted composition).

Preferably, in step b) the agrochemical formulation, a liquid carrier (e.g. water) and the adjuvant are contacted. The sequence of contacting the agrochemical formulation, liquid carrier and adjuvant may be any one. This usually results in a sprayable, aqueous composition.

In step b) the weight ratio of the agrochemical formulation (which might be a liquid or solid) and the liquid carrier (e.g. water) is typically in the range of 1:1 to 1:1000, preferably 1:2 to 1:1000, more preferably 1:5 to 1:1000, and especially 1:10 to 1:1000.

In another preferred embodiment, the method according to the invention comprises the step of contacting the adjuvant and the pesticide, wherein the pesticide is present in a concentration of less than 10 wt % in the resulting composition containing the adjuvant and the pesticide (preferably in the adjuvanted composition resulting in step b)). The pesticide is preferably present in a concentration of less than 5 wt %, more preferably less than 2.5 wt %, even more preferred less 1 wt %, and especially less than 0.5 wt % in the adjuvanted composition pesticide (preferably in the adjuvanted composition resulting in step b)).

The term "sprayable" composition refers to compositions which may be sprayed by usual agrochemical spraying equipment. Sprayable composition usually have a low dynamic viscosity at 20° C., such as below 30 mPas, preferably below 10 mPas, more preferably below 3 mPas, and in particular below 1.5 mPas. Sprayable compositions usually contains no solid particles or very small particles. Typically, the D50 particle size is below 50 µm, preferably below 20 µm, and in particular below 10µ. In a further embodiment, at least 90% of the particles have a particle size of below 50 µm, preferably below 25 µm.

The application rate of the sum of adjuvant and pesticide is typically from 2 g/ha to 100 kg/ha, preferably from 50 g/ha to 10 kg/ha, and especially from 200 g/ha to 5 kg/ha.

The method according to the invention utilizes a pesticide, which may be dissolved and/or dispersed in water. Preferably, the pesticide is dissolved and/or dispersed (preferably dissolved) in the adjuvanted composition, e.g. resulting from step b).

The method according to the invention is a method for enhancing the performance of a pesticide. The term "enhancing" means that the performance is better compared to the comparable method without the adjuvant. The term "performance" means any type of property of a pesticide, such as biological activity, crop selectivity, phytotoxicity, ecotoxicity, human toxicity, storage stability, or a reduction of volatility.

The present invention further relates to a composition comprising an auxin-herbicide and an adjuvant, which contains a guanidine of the formula (A) and/or salts thereof, as defined above. Preferred embodiments, e.g. regarding $R^1$, $R^2$, $R^3$, $R^4$, $R^5$, $R^6$, $R^7$, $R^8$, m, n and x are as described above. Preferred auxin-herbicides, such as synthetic and natural auxin herbicides, are mentioned above. Especially preferred auxin herbicides are 2,4-D and its salts and esters, and dicamba and its salts and esters, wherein 2,4-D and dicamba are more preferred. Most preferred auxin herbicide is dicamba and its salts.

The composition according to the invention, the agrochemical formulation or the adjuvanted composition may comprise at least one further pesticide. The further pesticide can be selected from the group consisting of fungicides, insecticides, nematicides, herbicide and/or safener or growth regulator, preferably from the group consisting of fungicides, insecticides or herbicides, more preferably herbicides. Preferred further pesticides are imidazolinone herbicides and triazine herbicides. The further pesticides are preferably free of an anionic pesticide.

The composition and method according to the invention are suitable as herbicides. They are suitable as such or as an appropriately formulated composition. The composition and method according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

Depending on the application method in question, the compositions and method according to the invention can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Brassica juncea, Brassica campestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum,* Triticale, *Triticum durum, Vicia faba, Vitis vinifera, Zea mays.*

Preferred crops are: *Arachis hypogaea, Beta vulgaris* spec. *altissima, Brassica napus* var. *napus, Brassica oleracea, Brassica juncea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), Triticale, *Triticum aestivum, Triticum durum, Vicia faba, Vitis vinifera* and *Zea mays*

The composition and method according to the invention can also be used in genetically modified plants, e.g. to alter their traits or characteristics. The term "genetically modified plants" is to be understood as plants, which genetic material has been modified by the use of recombinant DNA techniques in a way that under natural circumstances it cannot readily be obtained by cross breeding, mutations, natural recombination, breeding, mutagenesis, or genetic engineering. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, are particularly useful with the composition and method according to the invention. Tolerance to classes of herbicides has been developed such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase (PPO) inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Examples of these herbicide resistance technologies are also described in US 2008/0028482, US2009/0029891, WO 2007/143690, WO 2010/080829, U.S. Pat. No. 6,307,129, U.S. Pat. No. 7,022,896, US 2008/0015110, U.S. Pat. No. 7,632,985, U.S. Pat. No. 7,105,724, and U.S. Pat. No. 7,381,861, each herein incorporated by reference.

Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate, dicamba, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Furthermore, it has been found that the composition and method according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the composition and method according to the invention.

As desiccants, the composition and method according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval in which the individual cotton plants mature leads to an increased fiber quality after harvesting.

The composition and method according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal compositions may also be applied by the low-volume or the ultra-low-volume method, or in the form of microgranules.

The composition and method according to the invention can be applied pre- or post-emergence, or together with the seed of a crop plant. It is also possible to apply the compounds and compositions by applying seed, pretreated with a composition of the invention, of a crop plant. If the active compounds A and C and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the composition or method according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the composition and method according to the invention. Here, the herbicidal compositions can be applied diluted or undiluted.

The term seed comprises seed of all types, such as, for example, corns, seeds, fruits, tubers, seedlings and similar forms. Here, preferably, the term seed describes corns and seeds.

The seed used can be seed of the useful plants mentioned above, but also the seed of trans-genic plants or plants obtained by customary breeding methods.

The rates of application of the active compound are from 0.0001 to 3.0, preferably 0.01 to 1.0 kg/ha of active substance (a.s.), depending on the control target, the season, the target plants and the growth stage. To treat the seed, the pesticides are generally employed in amounts of from 0.001 to 10 kg per 100 kg of seed.

Moreover, it may be advantageous to apply the compositions of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

The composition according to the invention can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention. Examples for composition types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF). Usually the composition types (e.g. SC, OD, FS, EC, WG, SG, WP, SP, SS, WS, GF) are employed diluted. Composition types such as DP, DS, GR, FG, GG and MG are usually used undiluted. The compositions are prepared in a known manner. When the agrochemical composition is an aqueous composition, the salt according to the invention may dissociate into anions and cations.

The composition according the invention is preferably a agrochemical composition in the form of a soluble concentrate (SL), oil dispersion (OD), water-soluble granule (SG), or water-soluble powder (SP).

The agrochemical compositions may also comprise auxiliaries which are customary in agrochemical compositions. The auxiliaries used depend on the particular application form and active substance, respectively. Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols (such as ethylene glycol or 1,2-propylene glycol), ketones such as cyclohexanone and gamma-butyrolactone, fatty acid dimethylamides, fatty acids and fatty acid esters and strongly polar solvents, e.g. amines such as N-methylpyrrolidone. Preferred solvent is water.

Solid carriers are mineral earths such as silicates, silica gels, talc, kaolins, limestone, lime, chalk, bole, loess, clays, dolomite, diatomaceous earth, calcium sulfate, magnesium sulfate, iron sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wetters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkylarylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof. Further suitable surfactants (especially for agrochemical compositions comprising glyphosate) are alkoxylated $C_{4-22}$-alkylamines, such as ethoxylated tallow amine (POEA) and the surfactans disclosed in EP1389040 (e.g. those in Examples 1 to 14).

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA). Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie). Examples for suitable anti-freezing agents are ethylene glycol, propylene glycol, urea and glycerin. Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof. Examples for tackifiers or binders are polyvinylpyrrolidons, polyvinylacetates, polyvinyl alcohols and cellulose ethers (Tylose®, Shin-Etsu, Japan). Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Powders, materials for spreading and dusts can be prepared by mixing or concomitantly grinding the salts according to the invention and, if appropriate, further active substances, with at least one solid carrier. Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for Composition Types are:
1. Composition Types for Dilution with Water
i) Water-Soluble Concentrates (SL, LS)

50 parts by weight of a pesticide are dissolved in 50 parts by weight of water or in a water-soluble solvent. As an alternative, wetting agents or other auxiliaries are added. The active substance dissolves upon dilution with water. In this way, a composition having a content of 10% by weight of active substance is obtained.

ii) Dispersible Concentrates (DC)

20 parts by weight of a pesticide are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable Concentrates (EC)

15 parts by weight of a pesticide are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of a pesticide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of a pesticide are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-Dispersible Granules and Water-Soluble Granules (WG, SG)

50 parts by weight of a pesticide are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-Dispersible Powders and Water-Soluble Powders (WP, SP, SS, WS)

75 parts by weight of a pesticide are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of a pesticide are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition Types to be Applied Undiluted
ix) Dustable Powders (DP, DS)

5 parts by weight of a pesticide are ground finely and mixed intimately with 95 parts by weight of finely divided kaolin. This gives a dustable composition having an active substance content of 5% by weight.

x) Granules (GR, FG, GG, MG)

0.5 parts by weight of a pesticide is ground finely and associated with 99.5 parts by weight of carriers. Current methods are extrusion, spray-drying or the fluidized bed. This gives granules to be applied undiluted having an active substance content of 0.5% by weight.

xi) ULV Solutions (UL)

10 parts by weight of a pesticide are dissolved in 90 parts by weight of an organic solvent, e.g. xylene. This gives a composition to be applied undiluted having an active substance content of 10% by weight.

The composition types i), iv), vii) and x) are preferred. The composition type i) is especially preferred.

The agrochemical compositions generally comprise between 0.01 and 95%, preferably between 0.1 and 90%, most preferably between 0.5 and 90%, by weight of a pesticide. These active substances are employed in a purity of from 90% to 100%, preferably from 95% to 100% (according to NMR spectrum). Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations.

Very suitable agrochemical compositions of the salts according to the invention are:

a) Water-Soluble Concentrate
   10-70 wt % herbicidal salt and optionally at least one further pesticide, 30-90 wt % water, and optionally up to 10 wt % auxiliaries, such as surfactants, thickeners, or colorants, wherein the amount of all components adds up to 100 wt %.

b) Wettable-Powder
   10-90 wt % herbicidal salt and optionally at least one further pesticide, 9-80 wt % solid carrier, 1-10 wt % surfactant, and optionally auxiliaries, wherein the amount of all components adds up to 100 wt %.

c) Water Dispersable Granules
   10-90 wt % herbicidal salt and optionally at least one further pesticide, 9-80 wt % solid carrier, 1-10 wt % surfactant, and optionally auxiliaries, wherein the amount of all components adds up to 100 wt %.

d) Granules
   0.5-20 wt % herbicidal salt and optionally at least one further pesticide, 0.5-20 wt % solvent, 40-99 wt % solid carrier, and optionally auxiliaries, wherein the amount of all components adds up to 100 wt %.

In a further preferred embodiment, the composition according to the invention is a herbicidal salt comprising an anionic form of the auxin-herbicide and a cationic form of the adjuvant, which is a guanidine of the formula (A). The herbicidal salt may contain at least 80 wt %, preferably at least 90 wt % and in particular at least 97 wt % of the sum of the anionic form of the auxin-herbicide and the cationic form of the adjuvant. The herbicidal salt may comprise further anions or cations.

The cationic form of the adjuvant usually is a guanidinium cation as represented by the following formula:

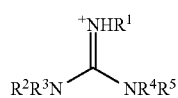

Preferred examples of guanidinium cations are guanidinium ($R^1$, $R^2$, $R^3$, $R^4$, and $R^5$ are H), and cations of dodine and iminoctadine.

Preferred examples of anionic forms of the auxin-herbicide may be selected from anions of above listed synthetic and natural auxin herbicides, wherein synthetic auxin herbicides are preferred. More preferred anionic forms of the auxin-herbicides are anions from 2,4-D, 2,4-DB, aminopyralid, benazolin, chloramben, clomeprop, clopyralid, dicamba, dichlorprop, dichlorprop-P, fluoroxypyr, MCPA, MCPB, mecoprop, mecoprop-P, picloram, quinclorac, quinmerac, TBA (2,3,6), triclopyr, and aminocyclopyrachlor. Among these anions, 2,4-D and dicamba are especially preferred, wherein dicamba is most preferred.

The herbicidal salt comprises preferably an anionic form of 2,4-D, 2,4-DB, aminopyralid, benazolin, chloramben, clomeprop, clopyralid, dicamba, dichlorprop, dichlorprop-P, fluoroxypyr, MCPA, MCPB, mecoprop, mecoprop-P, picloram, quinclorac, quinmerac, TBA (2,3,6), triclopyr, or aminocyclopyrachlor, and a cationic form of guanidine, namely the guanidinium cation. The herbicidal salt is more preferably a salt of the anionic form of dicamba and guanidinium cation.

The herbicidal salt can be converted into customary types of agrochemical compositions, such as those described above. Preferred agrochemical compositions containing the herbicidal salt are soluble concentrate (SL), oil dispersion (OD), water-soluble granule (SG), or water-soluble powder (SP).

The application can be carried out before or during sowing. Methods for applying or treating agrochemical compounds and compositions thereof, respectively, on to plant propagation material, especially seeds, are known in the art, and include dressing, coating, pelleting, dusting, soaking and in-furrow application methods of the propagation material. In a preferred embodiment, the compounds or the compositions thereof, respectively, are applied on to the plant propagation material by a method such that germination is not induced, e.g. by seed dressing, pelleting, coating and dusting. In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The composition according to the invention can be used as such or in the form of their agrochemical compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention. Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water. The active substance concentrations in the ready-to-use preparations can be varied within relatively wide ranges. In general, they are from 0.0001 to 10%, preferably from 0.001 to 1% by weight of active substance. The active substances may also be used successfully in the ultra-low-volume process (ULV), it being possible to apply compositions comprising over 95% by weight of active substance, or even to apply the active substance without additives.

When employed in plant protection, the amounts of active substances, e.g. the herbicidal salt, applied are, depending on the kind of effect desired, from 0.001 to 5 kg per ha, preferably from 0.005 to 2 kg per ha, more preferably from 0.05 to 0.9 kg per ha, in particular from 0.1 to 0.75 kg per ha. In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required. When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1. Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The pesticide can also be present together with other active substances, e.g. with herbicides, insecticides, growth regulators, fungicides or else with fertilizers, as pre-mix or, if appropriate, not until immediately prior to use (tank mix).

The present invention also relates to a method for preparing the composition according to the invention comprising the step of contacting the auxin-herbicide and the adjuvant. They may be combined either neatly or in its available formulation, for example, dry or solid formulations, as well as liquid formulations such as aqueous formulations. Preferably, the auxin-herbicide and the adjuvant are contacted in water. The water may be removed after the combining for isolation of the herbicidal salt. The combination may be done at usual temperature such as from −20° C. to 100° C., preferably from 3° C. to 90° C.

The present invention also relates to a method of combating harmful insects and/or phytopathogenic fungi, which comprises contacting plants, seed, soil or habitat of plants in or on which the harmful insects and/or phytopathogenic fungi are growing or may grow, plants, seed or soil to be protected from attack or infestation by said harmful insects and/or phytopathogenic fungi with an effective amount of the composition according to the invention. The anionic pesticides comprises usually an insecticide and/or an fungicide. For example, for combating harmful insects the agrochemical formulation comprises an insecticide. For example, for combating phytopathogenic fungi the agrochemical formulation comprises a fungicide.

The present invention further relates to a method of controlling undesired vegetation, which comprises allowing a herbicidal effective amount of the composition according to the invention to act on plants, their habitat or on seed of said plants. In a preferred embodiment, the method may also include plants that have been rendered tolerant to the application of the agrochemical formulation wherein the anionic pesticide is a herbicide. The methods generally involve applying an effective amount of the agrochemical formulation of the invention comprising a selected herbicide to a cultivated area or crop field containing one or more crop plants which are tolerant to the herbicide. Although any undesired vegetation may be controlled by such methods, in some embodiments, the methods may involve first identifying undesired vegetation in an area or field as susceptible to the selected herbicide. Methods are provided for controlling the undesired vegetation in an area of cultivation, preventing the development or the appearance of undesired vegetation in an area of cultivation, producing a crop, and increasing crop safety. Undesired vegetation, in the broadest sense, is understood as meaning all those plants which grow in locations where they are undesired, which include but is not limited to plant species generally regarded as weeds.

In addition, undesired vegetation can also include undesired crop plants that are growing in an identified location. For example, a volunteer maize plant that is in a field that predominantly comprises soybean plants can be considered undesirable. Undesired plants that can be controlled by the methods of the present invention include those plants that were previously planted in a particular field in a previous season, or have been planted in an adjacent area, and include crop plants including soybean, corn, canola, cotton, sunflowers, and the like. In some aspects, the crop plants can be tolerant of herbicides, such as glyphosate, ALS-inhibitors, or glufosinate herbicides. The methods comprise planting the area of cultivation with crop plants which are tolerant to the herbicide, and in some embodiments, applying to the crop, seed, weed, undesired plant, soil, or area of cultivation thereof an effective amount of an herbicide of interest. The herbicide can be applied at any time during the cultivation of the tolerant plants. The herbicide can be applied before or after the crop is planted in the area of cultivation. Also provided are methods of controlling glyphosate tolerant weeds or crop plants in a cultivated area comprising applying an effective amount of herbicide other than glyphosate to a cultivated area having one or more plants that are tolerant to the other herbicide.

The term "herbicidal effective amount" denotes an amount of pesticidal active component, such as the salts or the further pesticide, which is sufficient for controlling undesired vegetation and which does not result in a substantial damage to the treated plants. Such an amount can vary in a broad range and is dependent on various factors, such as the species to be controlled, the treated cultivated plant or material, the climatic conditions and the specific pesticidal active component used.

The term "controlling weeds" refers to one or more of inhibiting the growth, germination, reproduction, and/or proliferation of; and/or killing, removing, destroying, or otherwise diminishing the occurrence and/or activity of a weed and/or undesired plant.

The composition or method according to the invention has excellent herbicidal activity against a broad spectrum of economically important monocotyledonous and dicotyledonous harmful plants, such as broad-leaved weeds, weed grasses or Cyperaceae. The active compounds also act efficiently on perennial weeds which produce shoots from rhizomes, root stocks and other perennial organs and which are difficult to control. Specific examples may be mentioned of some representatives of the monocotyledonous and dicotyledonous weed flora which can be controlled by the composition or method according to the invention, without the enumeration being restricted to certain species. Examples of weed species on which the herbicidal compositions act efficiently are, from amongst the monocotyledonous weed species, *Avena* spp., *Alopecurus* spp., *Apera* spp., *Brachiaria* spp., *Bromus* spp., *Digitaria* spp., *Lolium* spp., Echinochloa spp., *Leptochloa* spp., *Fimbristylis* spp., *Panicum* spp., *Phalaris* spp., *Poa* spp., *Setaria* spp. and also *Cyperus* species from the annual group, and, among the perennial species, *Agropyron, Cynodon,*

*Imperata* and *Sorghum* and also perennial *Cyperus* species. In the case of the dicotyledonous weed species, the spectrum of action extends to genera such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. *Eclipta* spp., *Sesbania* spp., *Aeschynomene* spp. and *Viola* spp., *Xanthium* spp. among the annuals, and *Convolvulus, Cirsium, Rumex* and *Artemisia* in the case of the perennial weeds.

The present invention further relates to seed comprising the composition according to the invention. Preferably, the seed is coated with an agrochemical formulation comprising the composition according to the invention.

The present invention further relates to a use of the adjuvant as defined above for enhancing the performance of a pesticide as defined above. Preferably, the biological activity is enhanced. In another preferred embodiment, the volatility of the pesticide is reduced.

The present invention offers various advantages: The method and the composition according to the invention results in a low volatility of the pesticide. Further on, the composition according to the invention is easily prepared starting from cheap, industrially available compounds, which are easy to handle. The pesticidal activity remains at a level equivalent to known salts or the free acid of the pesticide. The invention reduces off-target crop injury due to the reduced volatility, even without adversely affecting the pesticidal activity. The low volatility characteristics are maintained whether delivered as a tank mix or pre-mix formulation. Further on, the invention increases the physical stability of the composition, e.g. by reducing the tendency to crystallize or the tendency for phase separation. The guanidine of the formula (A) is available in industrial scale, is has a very low toxicity to humans, animals and the environment and a very low phytotoxicity.

The invention is further illustrated but not limited by the following examples.

EXAMPLES

Example 1

SL Formulation 5.9 g Guanidine is added under stirring at room temperature to a suspension of 22.1 g dicamba (free acid) in 200 ml water. The resulting solution may be used as SL formulation or optionally further auxiliaries may be added.

Example 2

Herbicidal Salt

In order to prepare a herbicidal salt of dicamba and guanidine, the water from the aqueous solution of Example 1 (without auxiliaries) is removed under vacuum at room temperature. The guanidinium salt of dicamba is isolated in high yield and purity.

Example 3

SL Formulation 13.9 g Triazabicyclodecene (1,5,7-Triazabicyclo[4.4.0]dec-5-ene or TBD) is added under stirring at room temperature to a suspension of 22.1 g dicamba (free acid) in 200 ml water. The resulting solution may be used as SL formulation or optionally further auxiliaries may be added.

Example 4

Tankmix 0.2 L of a SL formulation containing 22.1 g dicamba (free acid) are diluted at room temperature with 20 L of water to prepare a sprayable tank mix. To these 20.2 L of tank mix 5.9 g guanidine is added while stirring.

Example 5

Tankmix 0.2 L of a SL formulation containing 22.1 g dicamba (free acid) are diluted at room temperature with 80 L of water to prepare a sprayable tank mix. To these 80.2 L of tank mix 13.9 g triazabicyclodecene is added while stirring.

Example 6

Volatility

Soybeans are grown in pots to 1st trifoliate unfolded and 2nd trifoliate slightly expanded (approx 10 days from planting until ready for treatment). Two plants are placed in each treatment replicate, each consisting of a tray with 8 glass petri dishes (8×9 cm). The roots growing out of the pots are trimmed before placing in trays to avoid contact with petri dishes or volatility exposure.

The trays with the petri dishes are treated with 4480 g dicamba acid equivalents/ha (based on SL formulation of Example 1 or 3, or the tank mix of Example 4) and immediately cover with plastic dome. Next, the dome cover are quickly removed and two soybean plants are placed in the middle of each tray. A new dome cover is immediately used and fixed with binder clips at each end to hold dome on tray. A thermometer is included in the trays to monitor temperature. The dome tray units are covered with shade cloth if the temperature rises above 35° C. The percentage of injury (epinasty, cupping and growth reduction) is assessed 2, 7, 14, and 21 days later. For comparison, dicamba free acid or Banvel® (SL formulation of dicamba salt of dimethylamine (water-soluble concentrate 480 g/l, commercially available from Syngenta) are used at the same active dose rate instead of the dicamba salt from Example 3.

The dicamba salts according to the invention result in clearly less percentage of injury to the soybeans compared to the dicamba free acid or Banvel®.

We claim:
1. A method for reducing volatility of dicamba comprising contacting an adjuvant and dicamba, wherein the dicamba is present in a concentration of less than 10 wt % in the resulting composition containing the adjuvant and dicamba, and the adjuvant is present in an amount effective to reduce the volatility of dicamba, and wherein the adjuvant is selected from the group consisting of triazabicyclodecene, a guanidine of formula (A)

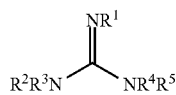

(A)

and a salt thereof, wherein
R$^1$, R$^2$, R$^3$, R$^4$ and R$^5$ are independently selected from the group consisting of H and C$_1$-C$_4$ alkyl.

2. The method of claim 1, wherein the dicamba is dissolved and/or dispersed in water.

3. The method of claim 1, wherein the resulting composition containing the adjuvant and dicamba is a sprayable aqueous composition.

4. The method of claim 1, wherein the dicamba is present in a concentration of less than 5 wt % in the resulting composition containing the adjuvant and dicamba.

5. The method of claim 1, wherein the adjuvant is soluble in water.

6. The method of claim 1, wherein the adjuvant is a solid.

7. The method of claim 1, wherein the adjuvant comprises a salt having an anionic counterion derived from an inorganic acid or an organic acid.

8. The method of claim 1, wherein the adjuvant comprises a salt having an anionic counterion selected from the group consisting of hydrogensulfate, phosphate, dihydrogenphosphate, monohydrogenphosphate, hydrocarbonate, and carbonate.

9. The method of claim 1, wherein R$^1$, R$^2$, R$^3$, R$^4$, and R$^5$ are H.

10. A composition comprising dicamba and an adjuvant, wherein the dicamba is present in a concentration of less than 10 wt % in the composition, and the adjuvant is present in an amount effective to reduce the volatility of dicamba, and wherein the adjuvant is selected from the group consisting of triazabicyclodecene, a guanidine of formula (A)

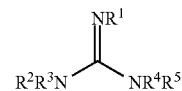

(A)

and a salt thereof, wherein
R$^1$, R$^2$, R$^3$, R$^4$ and R$^5$ are independently selected from the group consisting of H and C$_1$-C$_4$ alkyl.

11. The composition of claim 10, wherein the composition is an agrochemical composition in the form of a soluble concentrate (SL), oil dispersion (OD), water-soluble granule (SG), or water-soluble powder (SP).

12. The composition of claim 10, wherein the composition is a herbicidal salt comprising an anionic form of dicamba and a cationic form of the adjuvant.

13. The composition of claim 12, wherein the cationic form of the adjuvant is guanidinium cation.

14. A method of controlling undesired vegetation, which comprises treating plants, their habitat or seed of said plants a herbicidal effective amount of the composition of claim 10.

15. The method of claim 14, wherein the composition is an agrochemical composition in the form of a soluble concentrate (SL), oil dispersion (OD), water-soluble granule (SG), or water-soluble powder (SP).

16. The method of claim 14, wherein the composition is a herbicidal salt comprising an anionic form of the auxin-herbicide and a cationic form of the adjuvant.

\* \* \* \* \*